United States Patent
Lu et al.

(10) Patent No.: US 12,251,206 B2
(45) Date of Patent: Mar. 18, 2025

(54) METHOD, SYSTEM, AND COMPUTER PROGRAM PRODUCT FOR AUTOMATIC MULTI-OBJECT LOCALIZATION AND/OR VITAL SIGN MONITORING

(71) Applicant: Stichting IMEC Nederland, Eindhoven AE (NL)

(72) Inventors: Yiting Lu, Delft (NL); Marco Mercuri, Eindhoven (NL)

(73) Assignee: Stichting IMEC Nederland, AE Eindhoven (NL)

( * ) Notice: Subject to any disclaimer, the term of this patent is extended or adjusted under 35 U.S.C. 154(b) by 940 days.

(21) Appl. No.: 17/195,634

(22) Filed: Mar. 8, 2021

(65) Prior Publication Data

US 2021/0275035 A1    Sep. 9, 2021

(30) Foreign Application Priority Data

Mar. 9, 2020  (EP) ................................. 20161699
Jun. 5, 2020  (EP) ................................. 20178419

(51) Int. Cl.
| | |
|---|---|
| *A61B 5/024* | (2006.01) |
| *G16H 10/60* | (2018.01) |
| *G16H 40/60* | (2018.01) |
| *G16H 50/30* | (2018.01) |
| *G06F 17/14* | (2006.01) |

(52) U.S. Cl.
CPC .............. *A61B 5/024* (2013.01); *G16H 10/60* (2018.01); *G16H 40/60* (2018.01); *G16H 50/30* (2018.01); *G06F 17/142* (2013.01)

(58) Field of Classification Search
CPC ........ A61B 5/024; G16H 10/60; G16H 40/60; G06F 17/142
See application file for complete search history.

(56) References Cited

U.S. PATENT DOCUMENTS

| | | | | |
|---|---|---|---|---|
| 7,082,234 B2 * | 7/2006 | Lee | .................... | G02B 6/29394 |
| | | | | 385/24 |
| 10,436,888 B2 * | 10/2019 | Li | ......................... | G01S 13/886 |
| | | (Continued) | | |

FOREIGN PATENT DOCUMENTS

| | | |
|---|---|---|
| EP | 2525234 A1 | 11/2012 |
| EP | 3425419 A1 | 1/2019 |
| JP | 2014085763 A | 5/2014 |

OTHER PUBLICATIONS

Extended European Search Report in EP20178419.6 dated Nov. 30, 2020.

(Continued)

*Primary Examiner* — Baisakhi Roy
(74) *Attorney, Agent, or Firm* — MOSER TABOADA

(57) ABSTRACT

A method for automatic multi-object localization and/or vital sign monitoring is provided. The method comprises the steps of receiving a radar signal in order to form a corresponding observation matrix, reducing noise by applying singular value decomposition to the observation matrix, processing the result of the singular value decomposition by an independent component analysis in order to estimate the corresponding sources, and estimating propagation channels of the estimated sources by minimizing the corresponding residual error based on the observation matrix and the estimated sources.

15 Claims, 15 Drawing Sheets

(56) References Cited

U.S. PATENT DOCUMENTS

| | | | |
|---|---|---|---|
| 2007/0282203 A1* | 12/2007 | Baba | A61B 8/488 |
| | | | 600/453 |
| 2010/0152600 A1* | 6/2010 | Droitcour | A61B 5/7221 |
| | | | 600/534 |
| 2015/0369911 A1* | 12/2015 | Mabrouk | G01S 13/888 |
| | | | 342/159 |
| 2016/0150986 A1* | 6/2016 | Chen | G06T 7/0012 |
| | | | 382/128 |
| 2016/0220128 A1* | 8/2016 | Den Brinker | A61B 5/02055 |
| 2016/0259037 A1* | 9/2016 | Molchanov | G01S 7/0233 |
| 2017/0238805 A1* | 8/2017 | Addison | A61B 5/6843 |
| 2018/0196131 A1* | 7/2018 | Iizuka | G01S 13/003 |
| 2019/0350471 A1* | 11/2019 | Marks | A61B 5/0006 |
| 2020/0300972 A1* | 9/2020 | Wang | A61B 5/0002 |
| 2022/0022756 A1* | 1/2022 | Kiuru | G01S 13/56 |

OTHER PUBLICATIONS

Wang, et al., "A Hybrid FMCW—Interferometry Radar for Indoor Precise Positioning and Versatile Life Activity Monitoring", IEEE Transactions on Microwave Theory and Techniques, vol. 62, No. 11, Nov. 2014, 11 pages.

Adib, et al., "Multi-Person Localization via RF Body Reflections", Proceedings of the 12$^{th}$ USENIX Symposium on Networked Systems Design and Implementation (NSDI '15), May 4-6, 2015, Oakland, USA, pp. 1-14, 2015.

* cited by examiner

METHOD, SYSTEM, AND COMPUTER PROGRAM PRODUCT FOR AUTOMATIC MULTI-OBJECT LOCALIZATION AND/OR VITAL SIGN MONITORING

This application claims priority to European Application No. 20161699.2 filed on Mar. 9, 2020 and European Application No. 20178419.6 filed on Jun. 5, 2020, incorporated herein by reference.

The invention relates to a method for automatic multi-object localization and/or vital sign monitoring using radar, a system for automatic multi-object localization and/or vital sign monitoring using radar, and a computer program product comprising computer program code means adapted for automatic multi-object localization and/or vital sign monitoring using radar. The object can, for example, be people.

Generally, in times of an increasing number of older people, there is a growing need of contactless health monitoring in order to assist clinicians and caregivers in their daily work.

EP 3 425 419 A1 relates to a method for localization and monitoring of living being targets in an environment. Said method comprises the steps of transmitting a sequence of radio frequency waveforms, the waveforms being a continuous-wave waveform modulated in frequency and/or phase, and detecting a sequence of reflected waveforms being reflected by a target and Doppler-shifted due to a movement of the target, and forming a sequence of waveform transforms. The waveform transform comprises discretized information in a plurality of range bins. The information in a single range bin corresponds to reflections occurring at a specific sector in the environment. The information for a single specific sector in a sub-sequence of the sequence of waveform transforms is analyzed. Finally, the movement of a target in the specific sector based on the waveform transform information for that specific sector during a time period corresponding to the sub-sequence is detected. However, said method does not allow for automatic multi-object localization and/or vital sign monitoring in a particularly accurate and efficient manner.

Accordingly, there is an object to provide a method for automatic multi-object localization and/or vital sign monitoring, a system for automatic multi-object localization and/or vital sign monitoring using radar, and a computer program product comprising computer program code means adapted for automatic multi-object localization and/or vital sign monitoring.

This problem is solved by the features of claim 1 for a method for automatic multi-object localization and/or vital sign monitoring, the features of claim 14 for a system for automatic multi-object localization and/or vital sign monitoring using radar, and the features of claim 15 for a computer program product comprising computer program code means adapted for automatic multi-object localization and/or vital sign monitoring. The dependent claims contain further developments.

According to a first aspect of the invention, a method for automatic multi-object localization and/or vital sign monitoring is provided. The method comprises the steps of transmitting a radar signal, receiving a corresponding radar signal in order to form a corresponding observation matrix, reducing noise by applying singular value decomposition to the observation matrix, processing the result of the singular value decomposition by an independent component analysis in order to estimate the corresponding sources, and estimating propagation channels of the estimated sources by minimizing the corresponding residual error based on the observation matrix and the estimated sources. Advantageously, multiple objects, such as people, can automatically be localized and respective vital signs can be monitored in a highly accurate and efficient manner.

According to a first preferred implementation form of the first aspect of the invention, before the independent component analysis, the method further comprises the step of estimating the number of respective targets, preferably the number of respective persons, especially by calculating the signal-to-noise ratio of the respective uncorrelated sources in the result of the singular value decomposition. Advantageously, for example, inaccuracies can further be reduced.

According to a second preferred implementation form of the first aspect of the invention, the method further comprises the step of locating the respective objects and/or removing the respective order ambiguity on the basis of the estimated propagation channels. Advantageously, for instance, accuracy can further be increased.

According to a further preferred implementation form of the first aspect of the invention, the method further comprises the step of performing a phase demodulation with respect to the estimated sources. Advantageously, for example, inaccuracies can further be reduced. Further advantageously, the phase demodulation may preferably comprise or be a linear demodulation.

According to a further preferred implementation form of the first aspect of the invention, the method further comprises the step of extracting the respective vital signs information or signal from the estimated sources after the phase demodulation. Advantageously, for instance, both efficiency and accuracy can further be increased. Further advantageously, the respective vital sings information or signal may preferably comprise or be a time domain signal.

According to a further preferred implementation form of the first aspect of the invention, the step of extracting is performed on the basis of the following equation:

$$\hat{y}(t) = \hat{s}(t)\frac{\lambda_0}{4\pi},$$

wherein $\lambda_0$ denotes the corresponding wavelength at the first frequency of a respective chirp signal, and
wherein $\pi$ denotes the constant Pi.

Advantageously, for example, complexity can be reduced, which leads to an increased efficiency.

According to a further preferred implementation form of the first aspect of the invention, the method further comprises the step of obtaining the corresponding respiration and heartbeat signals by performing a filtering operation with respect to the respective vital signs information or signal. Advantageously, for instance, accuracy can further be increased.

According to a further preferred implementation form of the first aspect of the invention, the method further comprises the step of obtaining the corresponding respiration and heartbeat signals by performing a wavelet decomposition with respect to the respective vital signs information or signal. Advantageously, for example, inaccuracies can further be reduced.

According to a further preferred implementation form of the first aspect of the invention, the method further comprises the step of obtaining the corresponding respiration and heartbeat signals by performing a Hilbert transform followed by a convex optimization with respect to the respective vital signs information or signal. Advantageously, for instance, accuracy can further be increased.

According to a further preferred implementation form of the first aspect of the invention, the wavelet decomposition comprises the usage of a discrete Meyer mother-wavelet. Advantageously, for example, complexity can further be reduced, thereby increasing efficiency.

According to a further preferred implementation form of the first aspect of the invention, the method further comprises the step of estimating the corresponding heart rates by performing a frequency transform with respect to the respective respiration and heartbeat signals. Advantageously, for instance, inefficiencies can further be reduced.

According to a further preferred implementation form of the first aspect of the invention, the frequency transform comprises or is a fast Fourier transform. Advantageously, for example, by further reducing complexity, efficiency can be increased.

According to a further preferred implementation form of the first aspect of the invention, the radar signal comprises or is a chirp signal. Advantageously, for instance, accuracy can further be increased.

According to a further preferred implementation form of the first aspect of the invention, the radar signal originates from a frequency-modulated continuous wave radar, preferably a single input single output frequency-modulated continuous wave radar. Advantageously, for example, both efficiency and accuracy can further be increased. Further advantageously, instead of single input single output, it may be used multiple input multiple output or multiple input single output or single input multiple output. As a further advantage, any other type of modulated radar may be used.

According to a second aspect of the invention, a system for automatic multi-people localization and vital sign monitoring using radar is provided. The system comprises a transmitter unit, a receiving unit and a processing unit. In this context, the transmitting unit is configured to transmit a radar signal, the receiving unit is configured to receive a radar signal in order to form a corresponding observation matrix. In addition to this, the processing unit is configured to reduce noise by applying singular value decomposition to the observation matrix, to process the result of the singular value decomposition by an independent component analysis in order to estimate the corresponding sources, and to estimate propagation channels of the estimated sources by minimizing the corresponding residual error based on the observation matrix and the estimated sources. Advantageously, multiple objects, such as people, can automatically be localized and respective vital signs can be monitored in a highly accurate and efficient manner. Further advantageously, the processing unit may additionally be configured to estimate the number of respective targets, preferably the number of respective persons, especially by calculating the signal-to-noise ratio of the respective uncorrelated sources in the result of the singular value decomposition before the independent component analysis.

According to a third aspect of the invention, a computer program product is provided. The computer program product comprising computer program code means adapted for automatic multi-object localization and/or vital sign monitoring according to the steps of the method and of any of the preferred implementation forms thereof when said program is run on a computer or any electronic system. Advantageously, for example, multiple people can automatically be localized and respective vital signs can be monitored in a highly accurate and efficient manner.

Exemplary embodiments of the invention are now further explained with respect to the drawings by way of example only, and not for limitation. In the drawings.

Figure 1A:
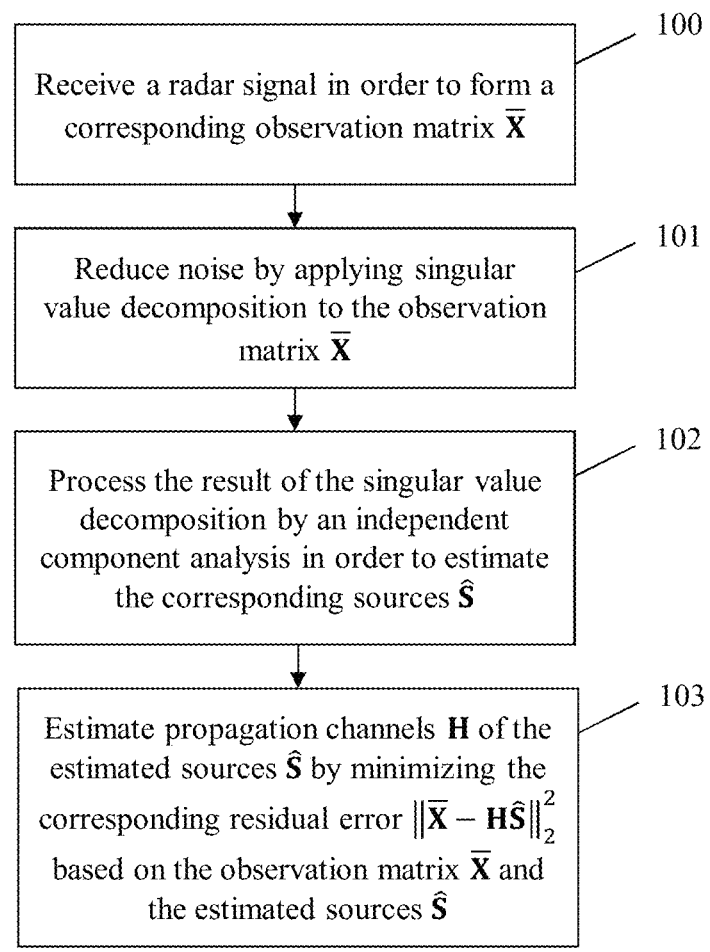
FIG. 1A shows a flow chart of an exemplary embodiment of the inventive method.

Firstly, FIG. 1A shows a flow chart of an embodiment of the inventive method for automatic multi-object localization and vital sign monitoring. In a first step 100, a radar signal is received in order to form a corresponding observation matrix $\overline{X}$. Then, in a second step 101, noise is reduced by applying singular value decomposition to the observation matrix $\overline{X}$. Furthermore, in a third step 102, the result of the singular value decomposition is processed by an independent component analysis in order to estimate the corresponding sources $\hat{S}$. Moreover, in a fourth step 103, propagation channels H of the estimated sources $\hat{S}$ are estimated by minimizing the corresponding residual error $\|\overline{X} - H\hat{S}\|_2^2$ based on the observation matrix $\overline{X}$ and the estimated sources $\hat{S}$.

It is noted that it might be particularly advantageous if the method further comprises the step of locating the respective targets and/or removing the respective order ambiguity on the basis of the estimated propagation channels Ĥ.

In addition to this or as an alternative, the method may further comprise the step of performing a phase demodulation with respect to the estimated sources Ŝ.

In this context, it might be particularly advantageous if the method further comprises the step of extracting the respective vital signs information or signal ŷ(t) from the estimated time domain sources ŝ(t) after the phase demodulation.

Further advantageously, the step of extracting may especially be performed on the basis of the following equation:

$$\hat{y}(t) = \hat{s}(t) \frac{\lambda_0}{4\pi}.$$

In this context, $\lambda_0$ denotes the corresponding wavelength at the first frequency of a respective chirp signal, and $\pi$ denotes the constant Pi. Moreover, the method may further comprise the step of obtaining the corresponding respiration and heartbeat signals by performing a filtering operation with respect to the respective vital signs information or signal ŷ(t).

It is further noted that the method may further comprise the step of obtaining the corresponding respiration and heartbeat signals by performing a wavelet decomposition with respect to the respective vital signs information or signal ŷ(t). It might be particularly advantageous if the method further comprises the step of obtaining the corresponding respiration and heartbeat signals by performing a Hilbert transform followed by a convex optimization with respect to the respective vital signs information or signal ŷ(t).

With respect to the above-mentioned wavelet decomposition, it is noted that the wavelet decomposition may preferably comprise the usage of a discrete Meyer motherwavelet.

Furthermore, the method may additionally or alternatively comprise the step of estimating the corresponding heart rates by performing a frequency transform with respect to the respective respiration and heartbeat signals. With respect to said frequency transform, it is noted that the frequency transform may preferably comprise or be a fast Fourier transform.

Moreover, with respect to the above mentioned radar signal, it is noted that the radar signal may preferably comprise or be a chirp signal. In addition to this or as an alternative, the radar signal may especially originate from a frequency-modulated continuous wave radar, preferably a single input single output frequency-modulated continuous wave radar.

Figure 1B:
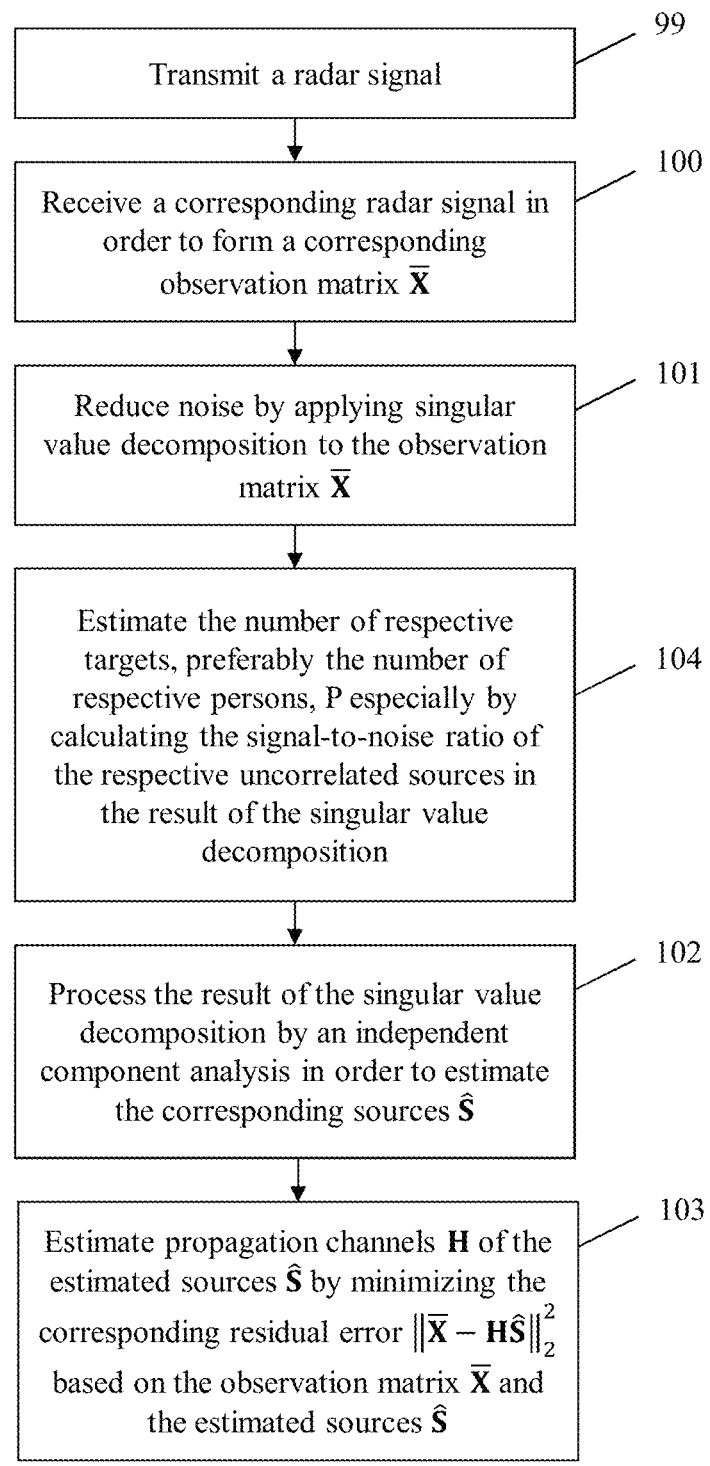
FIG. 1B shows a flow chart of a further exemplary embodiment of the inventive method.

Furthermore, FIG. 1B shows a flow chart of a further embodiment of the inventive method for automatic multi-object localization and vital sign monitoring. Said embodiment is based on the foregoing one according to FIG. 1A. Therefore, just the respective differences between these embodiments are explained in the following.

In this context, as a first step 99 (before the above-mentioned step 100), a radar signal is transmitted. In addition to this, especially in the sense of a target existence probability, between the above-mentioned steps 101 and 102, an additional step 104 has been inserted. As it can be seen from FIG. 1B, according to said step 104, before the independent component analysis of step 102, the number of respective targets, preferably the number of respective persons, P is estimated especially by calculating the signal-to-noise ratio of the respective uncorrelated sources in the result of the singular value decomposition of step 101.

Figure 2A:
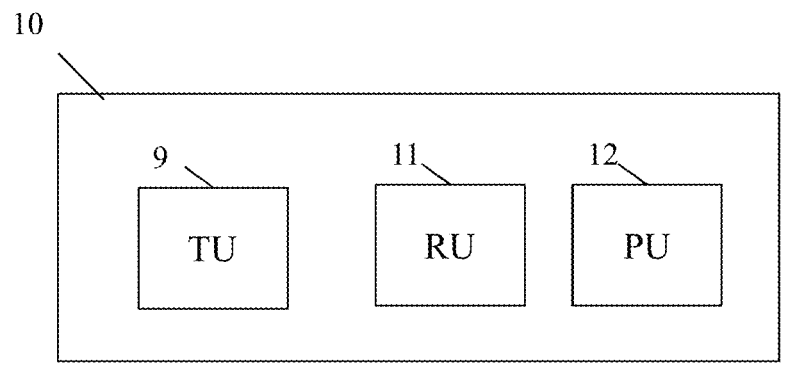
FIG. 2A shows an exemplary embodiment of an inventive system.

With respect to FIG. 2A, a block diagram of an exemplary embodiment of an inventive system 10 for automatic multi-object localization and vital sign monitoring is shown. According to FIG. 2A, the system 10 comprises a transmitting unit 9, receiving unit 11 and a processing unit 12. In this context, the transmitting unit 9 is configured to transmit a radar signal, the receiving unit 11 is configured to receive a corresponding radar signal in order to form a corresponding observation matrix $\overline{X}$. In addition to this, the processing unit 12 is configured to reduce noise by applying singular value decomposition to the observation matrix $\overline{X}$, to process the result of the singular value decomposition by an independent component analysis in order to estimate the corresponding sources Ŝ, and to estimate propagation channels H of the estimated sources Ŝ by minimizing the corresponding residual error $\|\overline{X} - H\hat{S}\|_2^2$ based on the observation matrix $\overline{X}$ and the estimated sources Ŝ.

Advantageously, especially in the sense of a target existence probability, the processing unit 12 may additionally be configured to estimate the number of respective targets, preferably the number of respective persons, P especially by calculating the signal-to-noise ratio of the respective uncorrelated sources in the result of the singular value decomposition before the independent component analysis.

It might be particularly advantageous if the processing unit 12 is further configured to locate the respective targets and/or removing the respective order ambiguity on the basis of the estimated propagation channels Ĥ. In addition to this or as an alternative, the processing unit 12 may preferably be configured to perform a phase demodulation with respect to the estimated sources Ŝ. In this context, the processing unit 12 of the system 10 may especially be configured to extract the respective vital signs information or signal ŷ(t) from the estimated time domain sources ŝ(t) after the phase demodulation.

It might be particularly advantageous if said extraction is performed on the basis of the following equation:

$$\hat{y}(t) = \hat{s}(t) \frac{\lambda_0}{4\pi},$$

wherein $\lambda_0$ denotes the corresponding wavelength at the first frequency of a respective chirp signal, and
wherein $\pi$ denotes the constant Pi.

In addition to this or as an alternative, the processing unit 12 may preferably be configured to obtain the corresponding respiration and heartbeat signals by performing a filtering operation with respect to the respective vital signs information or signal ŷ(t). Further additionally or further alternatively, the processing unit 12 may especially be configured to obtain the corresponding respiration and heartbeat signals by performing a wavelet decomposition with respect to the respective vital signs information or signal ŷ(t).

As a further alternative or in further addition to this, the processing unit 12 may especially be configured to obtain the corresponding respiration and heartbeat signals by performing a Hilbert transform followed by a convex optimization with respect to the respective vital signs information or signal ŷ(t).

With respect to the above-mentioned wavelet decomposition, it is noted that it might be particularly advantageous if the wavelet decomposition comprises the usage of a discrete Meyer mother-wavelet.

Again, with respect to the processing unit 12 of the system 10, it is noted that the processing unit 12 may additionally or alternatively be configured to estimate the corresponding heart rates by performing a frequency transform with respect to the respective respiration and heartbeat signals. In this context, with respect to said frequency transform, it is noted that it might be particularly advantageous if the frequency transform comprises or is a fast Fourier transform.

Furthermore, with respect to the radar signal, it is noted that the radar signal may preferably comprise or be a chirp signal.

In addition to this or as an alternative, the radar signal may especially originate from a frequency-modulated continuous wave radar, preferably a single input single output frequency-modulated continuous wave radar.

Figure 2B:
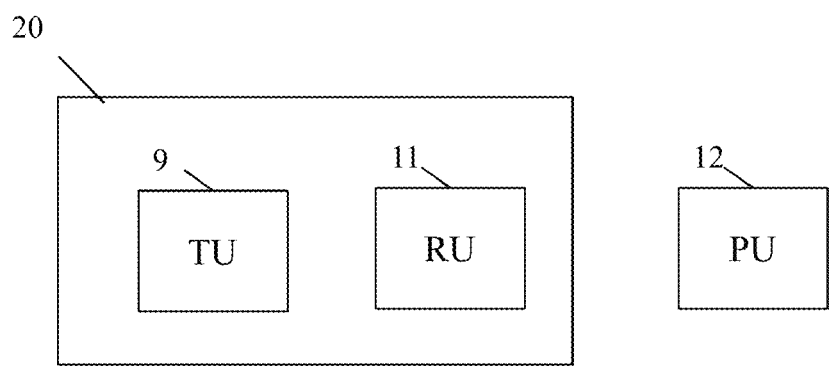
FIG. 2B shows a further exemplary embodiment of an inventive system.

With respect to FIG. 2B, a block diagram of a further exemplary embodiment of an inventive system 20 for automatic multi-object localization and vital sign monitoring is shown. Said embodiment is based on the foregoing one according to FIG. 2A. Therefore, just the respective differences between these embodiments are explained in the following.

In this context, whereas said system 20 comprises the already above-mentioned transmitter unit 9 and the receiving unit 11, the processing unit 12 is located outside the system 20.

Accordingly, FIG. 2B illustrates that the processing unit 12 can be far from the system 20 and/or in a different place. In addition to this or as an alternative, the processing unit can be embedded in a respective radar sensor.

Figure 3A:
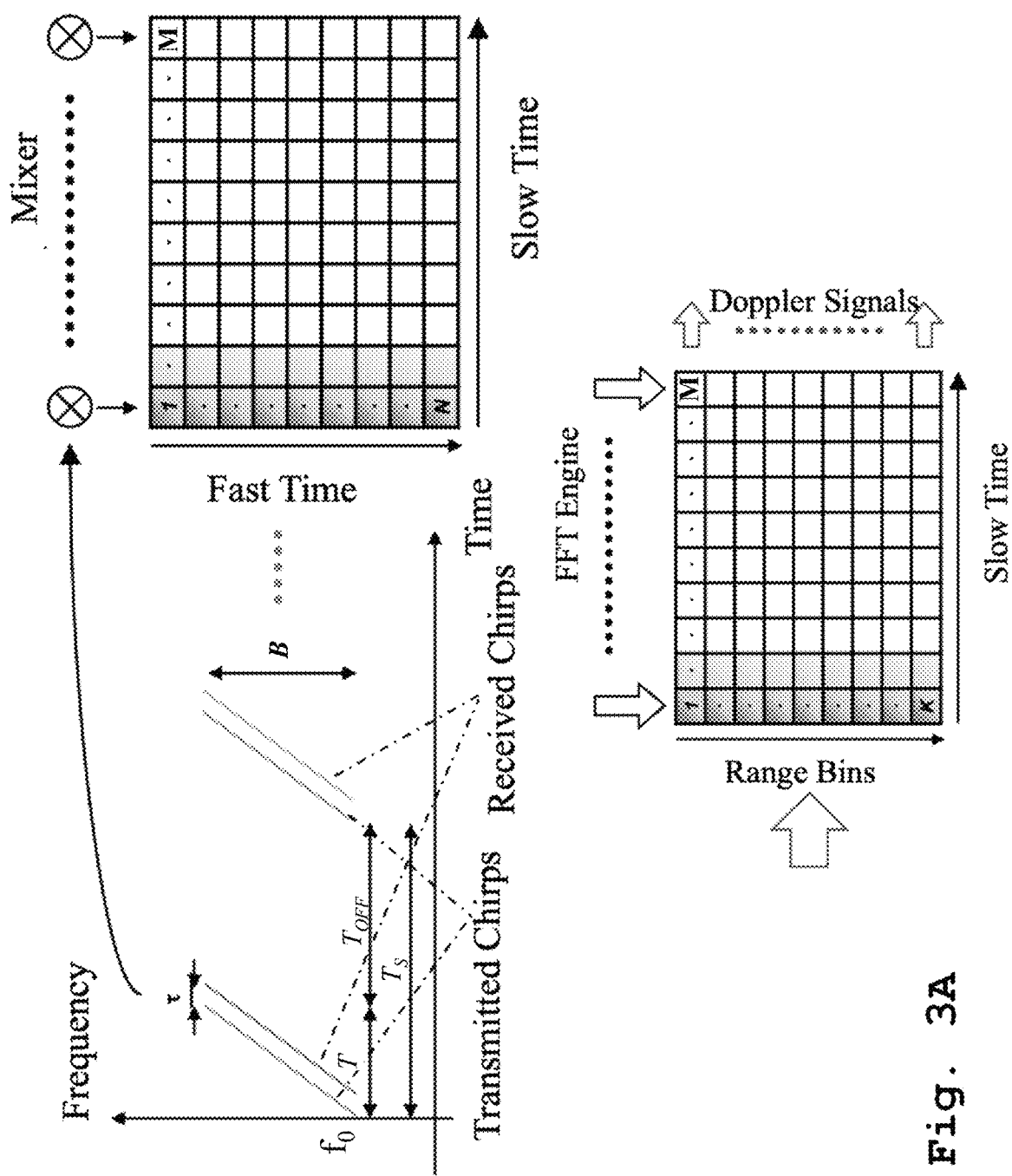
FIG. 3A shows of an exemplary generation of a data model matrix from frequency-modulated continuous wave radar signals.

In addition to the explanations above, the invention will be explained in more detail especially considering a frequency-modulated continuous wave (FMCW) radar in the following. However, the invention can be used with any radar with range-Doppler capability, for instance, stepped-frequency continuous wave (SFCW), phase-modulated continuous wave (PMCW), ultra-wideband impulse radio (UWB-IR) etc. A linear FMCW radar transmits a series of signals, called chirps, whose instantaneous frequency increases linearly over time as illustrated by FIG. 3A. Each chirp is T seconds long and is transmitted with a certain repetition interval Ts. No signal is transmitted during the time interval TOFF=Ts−T between two consecutive chirps.

It is noted that said time interval can be avoided so that the respective chirps are continuously transmitted without interruption.

The baseband signals (called beat signals), resulting by mixing the copies of the transmitted chirps with the received chirps, are digitized and arranged in a K×M data matrix, where K is the number of samples acquired per beat signal and depends both on T and on the sampling time Tf of the analog-to-digital converter (ADC) while M is the number of beat signals that are used in the data processing, collected each Ts. In radar terminology, Tf determines the fast time while Ts determines the slow time. This matrix is preprocessed by applying the fast Fourier transform (FFT) per column. The result is a K×M complex data matrix whose elements are denoted by X(k,m), with k=0, . . . , K−1 especially being the range bin index, K=N, and m=0, . . . , M−1 is the index in slow time.

The columns contain the range profiles, determined each Ts, while the rows contain the Doppler signals (i.e., phase shifts or vital signs information) from the range bins. This corresponds to ideally divide the whole radar detectable space (in radar terminology known as radar unambiguous range) into K evenly spaced concentric circles, namely range bins, whose size (i.e., range resolution) depends on the radar waveform. For example, it is to be considered an ideal situation with a single still subject at the k-th range bin in an empty room with no multipath. If it is scanned each row, and if we neglect the spreading effect of the FFT, there will be phase variations only at the k-th range bin. Exploiting especially this feature, we can determine the location of the target multiplying k by the range resolution and extract the vital signs from the complex signal in the k-th raw.

In indoor environments, the multipath interference cannot be ignored while designing a radar-based system. It occurs when a signal takes two or more paths from the transmitting antenna to the receiving antenna and depends on the room structure and the object's locations. This involves that the multipath signals generated by a subject may have identical delays (i.e., time of flight) of the direct path signals of one or more persons, causing false localizations and incorrect vital signs extraction. This is especially equivalent to saying that the multipaths and the direct paths signals comes from the same range bins.

The situation becomes even more problematic in presence of static reflectors (i.e., clutter, objects). Especially based on the limited room size, we consider only the first L range bins of the K total available ones. Within a range bin, differences in delays may be small and translated into phase shifts. Correspondingly, we assume that the number of possible path delays may preferably also be L. As a result, the (slowly time-varying) multipath propagation channel impulse response h(t,m) may be modeled as:

$$h(t, m) = \sum_{l=0}^{L-1} \beta_l \cdot \delta(t - \tau_l(m)), \quad (1)$$

wherein $\delta(\cdot)$ denotes the Dirac delta function, l denotes the path index, $\tau$ denotes the propagation of the l-th path, and $\beta$ denotes the complex path gain which indicates the overall attenuation and phase shift.

Figure 3B:
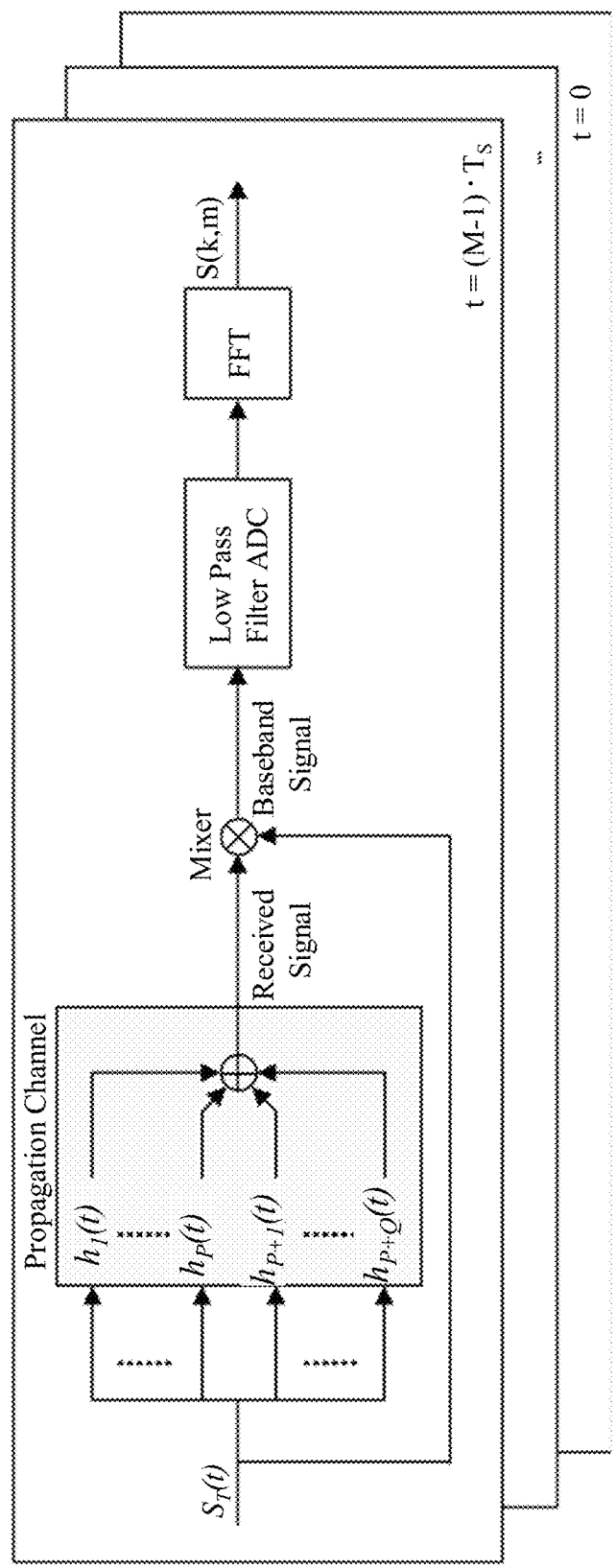
FIG. 3B shows an exemplary block diagram of the data model.

In this context, it is assumed that there are P people and Q static clutter in the room, which are regarded as point scatters and, therefore, the summation of all reflections from each infinitesimal point of a target's surface which falls into the same range bin can be regarded as one overall reflection through one propagation path. The only difference between the two types of targets is that the subjects have physiological activities (i.e., variable phase in slow time or Doppler signal), leading to a time varying $\tau l(m)$, while the static clutter involves a constant $\tau l$ (i.e., constant phase in slow time or Doppler signal). A sketch of this data model is shown in FIG. 3B.

The complex elements S(k,m) form a two-dimensional (2D) observation matrix X that can be decomposed as:

$$X = HS + C + N, \quad (2)$$

wherein H denotes an L×P complex mixing matrix, S denotes a P×M complex matrix containing the Doppler shifts (i.e., vital signs information) caused by the P subjects at each Ts, C denotes an L×M matrix with identical columns containing the DC (direct current) information in slow-time resulting from static reflections, and N denotes an L×M matrix containing zero mean additive noise.

The next step is to perform AC (alternate current) coupling to foregoing equation in order to remove the DC components (i.e., the mean values) while still preserving the physiological (i.e., variable) motions. After that, the observation matrix X becomes:

$$\overline{X} = H\overline{S} + N, \quad (3)$$

wherein the noise remains the same because of the zero-mean nature. The statistic properties of this data model especially are: (1) $\bar{S}$ has full rank P; (2) each row of $\bar{S}$ is regarded as an independent and zero mean source. All the signals are assumed to be random, independent, identically distributed (i.i.d.); (3) the noise is assumed to be additive, white, zero mean, complex Gaussian distributed, and independent from the sources.

It is noted that the model of the foregoing equation is especially used as starting point for the vital-sign monitoring and automatic localization in accordance with the invention.

Figure 4A:
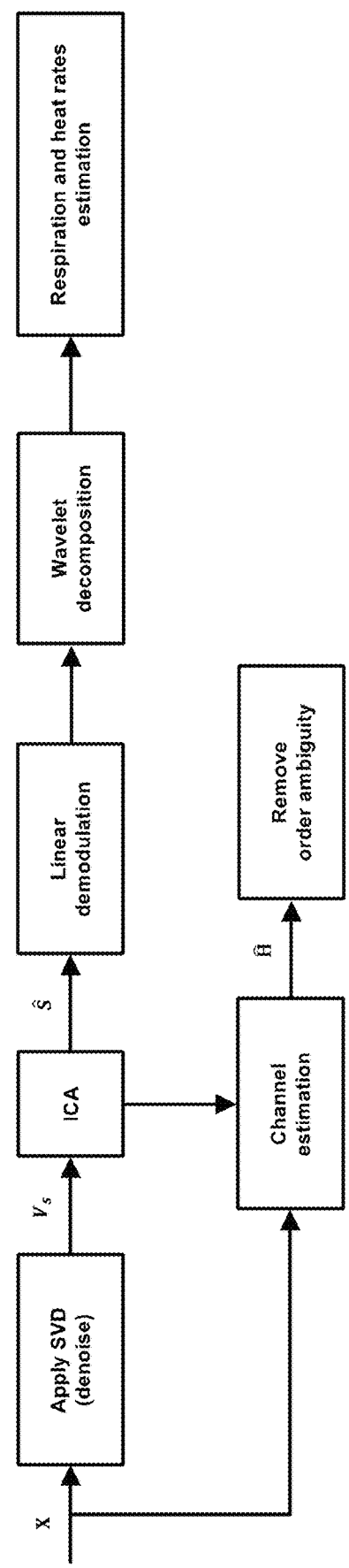
FIG. 4A shows a more abstracted kind of flow chart of an exemplary embodiment of the inventive method.

Another exemplary block diagram of the inventive method is shown in FIG. 4A. With the support of FIGS. 4B to 4H, this method is explained showing an example with two subjects, monitored for 20 seconds, sat on chairs and in front of desks, whose chest surfaces were respectively at 1.07 m and 2.26 m away from the radar.

In an ideal situation, with a range resolution of 20 cm, the Doppler information would be expected only in range bins 6 and 11 respectively for subject 1 and subject 2. However, as it can be seen in FIG. 4B, each range bin contains signals which can be direct paths, multipaths, or combinations of them. By a simple visual check, it results clear that the signals in bin 6 (which can be approximated as six sines in seconds) are also fairly replicated with different amplitudes and initial phases in bins 1-5, due to the leakage of the FFT, and also in bins 8-10, 14, 15, 17-19 due mainly to the multipath.

Similar considerations can be done for the signals of bin 11 (which can be considered as three sines in 20 seconds), which are replicated in bins 12-14, 16-19. In addition, the two subjects interfere each other in bins 14, 17-19 where the I signal corresponds to one subject while the Q signal corresponds to the other subject.

It is noted that some solutions have been proposed for automatic target localization based on vital signs according to the state of the art. Those approaches rely on the variation of the range spectrum to differentiate humans from stationary targets. The idea is that the physiological movements, involve a larger standard deviation (std) than static objects. Therefore, the range bins with large variations indicate the location of human targets. However, this approach fails in presence of multipaths, which result both in copies of the same target at wrong distances and in new (therefore false) targets when direct paths and multipaths combine in certain range bins.

Figure 4B:
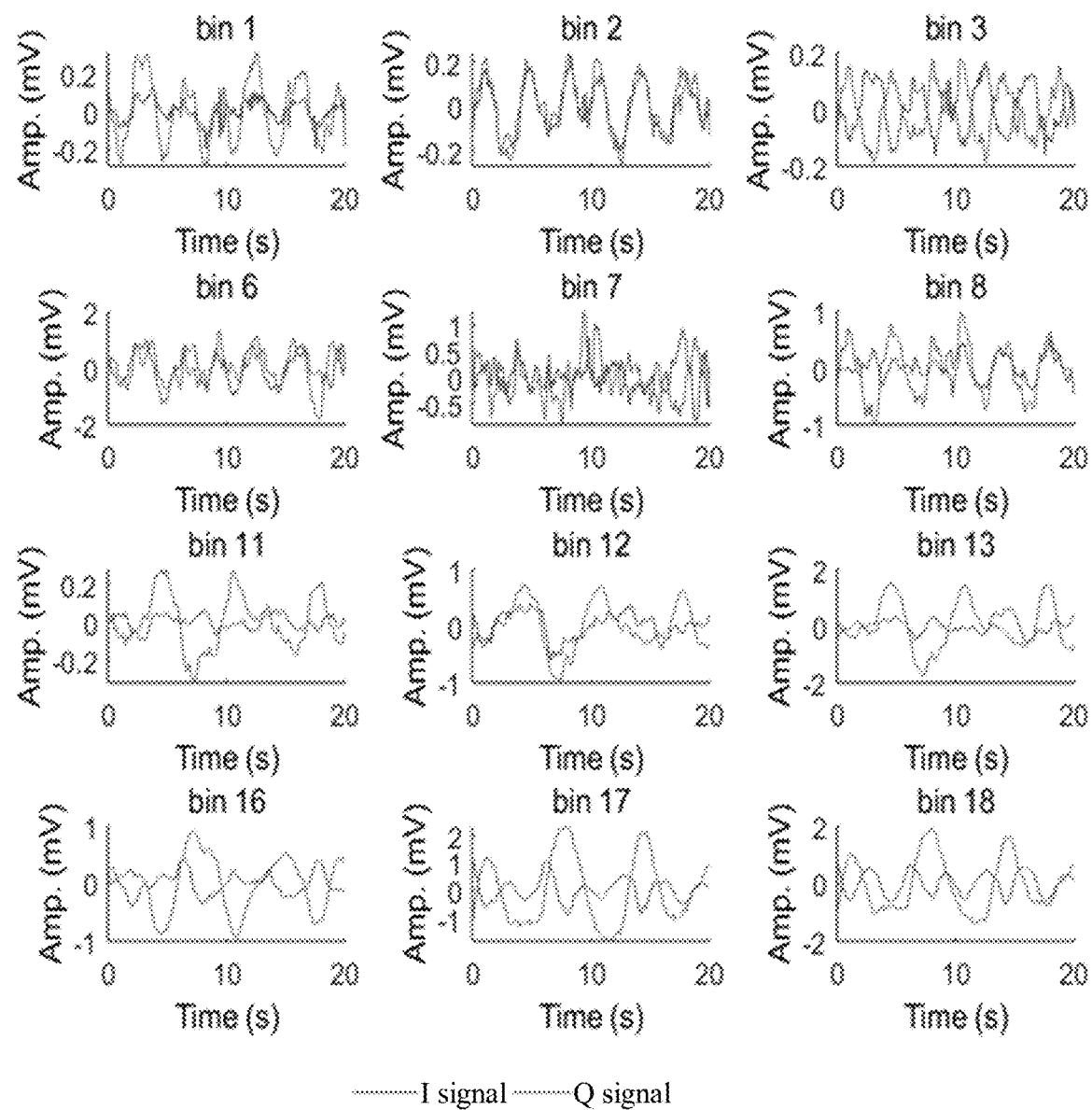
FIG. 4B shows exemplary in-phase and quadrature (IQ) signals extracted from first 20 range bins especially obtained after applying a fast Fourier transform to a K×M matrix.
Figure 4B:
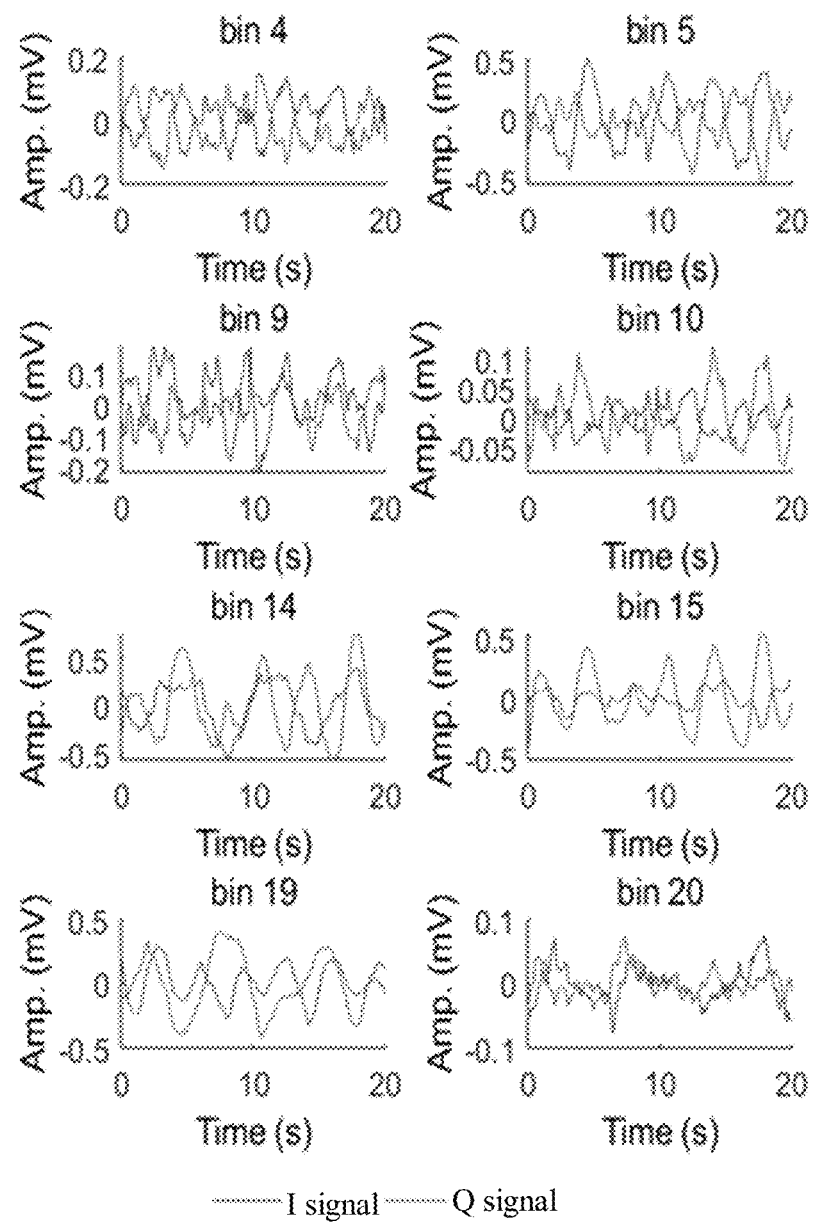
Figure 4C:
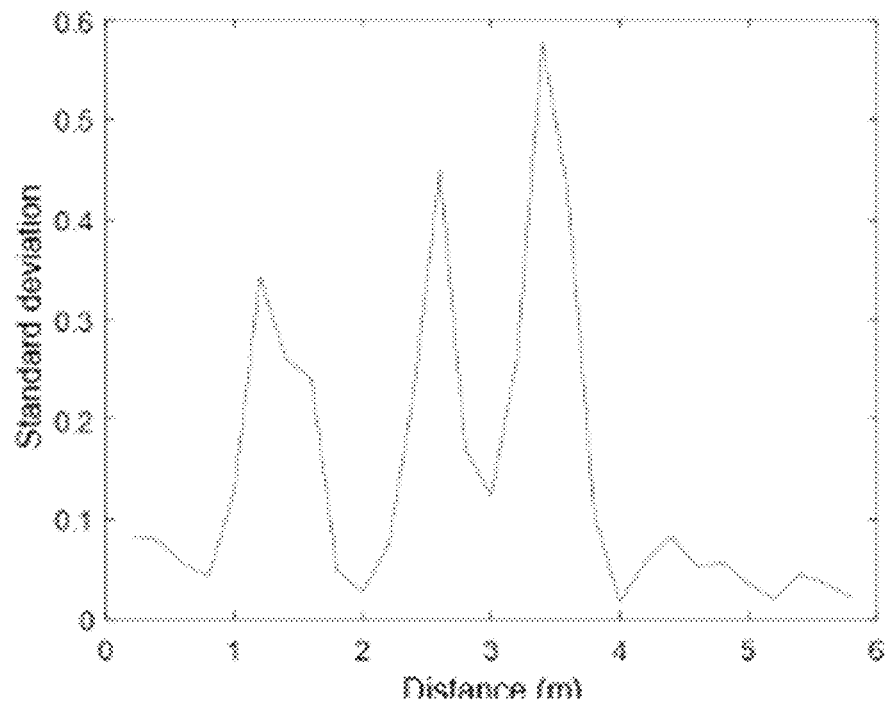
FIG. 4C shows an exemplary standard deviation profile obtained from the K×M matrix processed with the fast Fourier transform.

This is demonstrated by the standard deviation profile depicted in FIG. 4C, wherein the two highest peaks are respectively at 2.6 m (bin 13) and 3.4 m (bin 17), resulting therefore in a wrong localization. Actually, in this case, it is more probable to conclude that there are 3 persons. Looking at bin 13, it results that it contains the multipath signals (the copy) of subject 2.

Especially looking at bin 13 in FIG. 4B, it appears that it contains mainly the signals originated from subject 2 (i.e., 3 periods of a sinewave in 20 seconds). In this bin, the std response is especially higher than the one retrieved from the direct signal originated from the chest surface of subject 2 present in bin 11. This especially is a common result in real measurement condition and it can explained as it follows: the chest surface, containing both respiratory and heartbeat information, especially involves a smaller vibration than the one due to the abdomen which, depending on the radar positioning, can fall in adjacent bins and it does not contain heartbeat information. Bin 17, instead, especially results from the combination of two targets (I signal is mainly generated by subject 2 while Q signal by subject 1). In this bin, we especially report the highest std response. This is especially expected when multipaths (especially if generated by abdomen area) combine coherently.

With the aid of the invention, first the vital signs signals of the subjects are determined, and then they are located. In accordance with FIG. 4A, the first step is to reduce the noise by applying singular value decomposition (SVD) to $\bar{X}$. Its result is then processed by an independent component analysis (ICA) algorithm in order to estimate the sources $\hat{S}$. The vital signs information is preserved in the phase information of S. The AC coupling step used to obtain the above-mentioned equation $\bar{X}=H\bar{S}+N$ removes all the DC information of the target, resulting in a distortion in the phase (angle) extraction. Therefore, a phase demodulation has been used on $\hat{S}$ to perform phase demodulation in order to extract the vital signs information or signal $\hat{y}(m)$.

At this point, especially an order ambiguity issue has to be faced: it is not yet possible to indicate which source (i.e., vital signs signal) corresponds to which target. From the equation $\bar{X}=H\bar{S}+N$, H determines the linear combinations of the sources in $\bar{S}$, so the magnitudes of the elements in H indicate the energy of the sources in every range bin. Therefore, if one knows the propagation channels H of the sources one can localize the targets and also remove the order ambiguity. From the observation matrix $\bar{X}$ and the estimated source matrix $\hat{S}$, one can estimate $\hat{H}$.

Figure 4D:
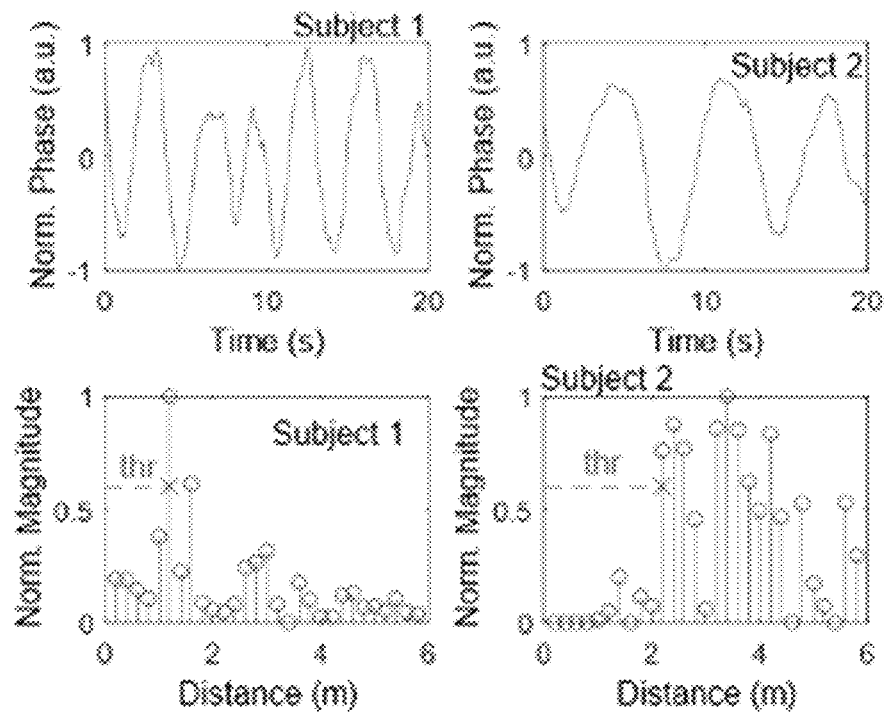
FIG. 4D shows exemplary vital signs signals (top) and channel responses (bottom) of two subjects.

FIG. 4D shows the determined vital signs signals and the corresponding channel responses by which the targets can be correctly located. In the channel responses, the outliers originated by additive noise are small and they can be easily excluded by setting a threshold thr (dashed line in FIG. 4D), while the outliers resulting from multipaths can be removed by detecting the shortest direct path (x in FIG. 4D). The respiration and heartbeat signals are obtained from the vital signs signals using the Wavelet decomposition (exemplarily, the Discrete Meyer mother wavelet has been chosen) and the corresponding rates were estimated using the FFT.

Figure 4E:
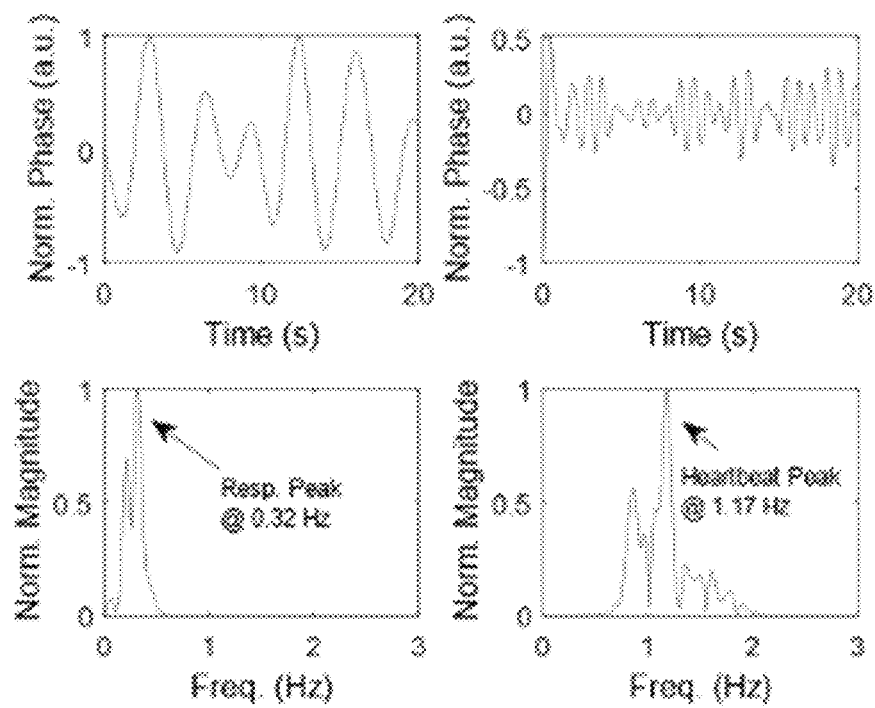
FIG. 4E shows exemplary respiration (left) and heartbeat (right) signals of the first subject and corresponding spectra obtained with the aid of the invention.
Figure 4F:
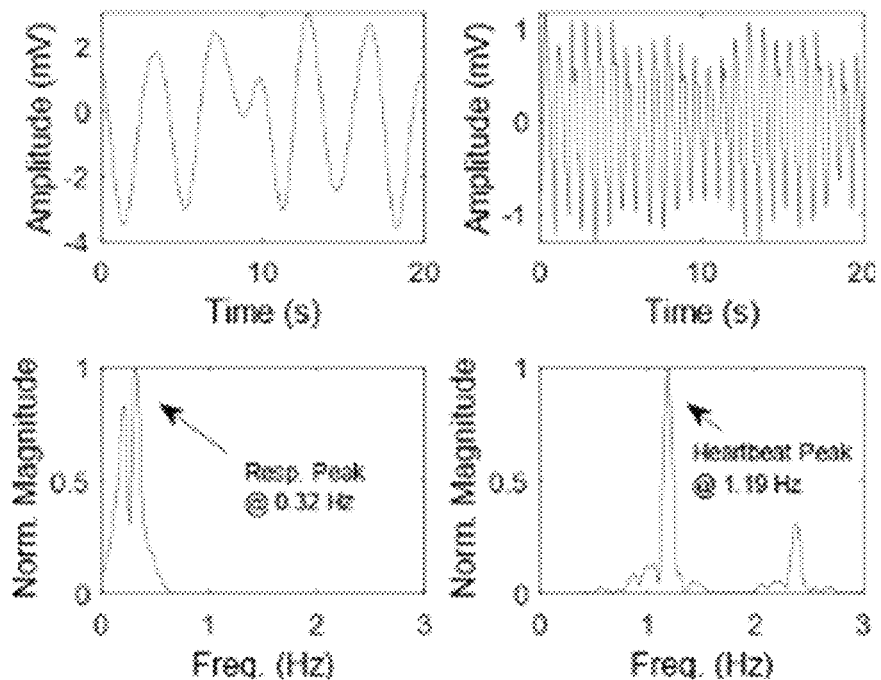
FIG. 4F shows exemplary respiration (left) and heartbeat (right) signals of the second subject and corresponding spectra obtained with the aid of the invention.
Figure 4G:
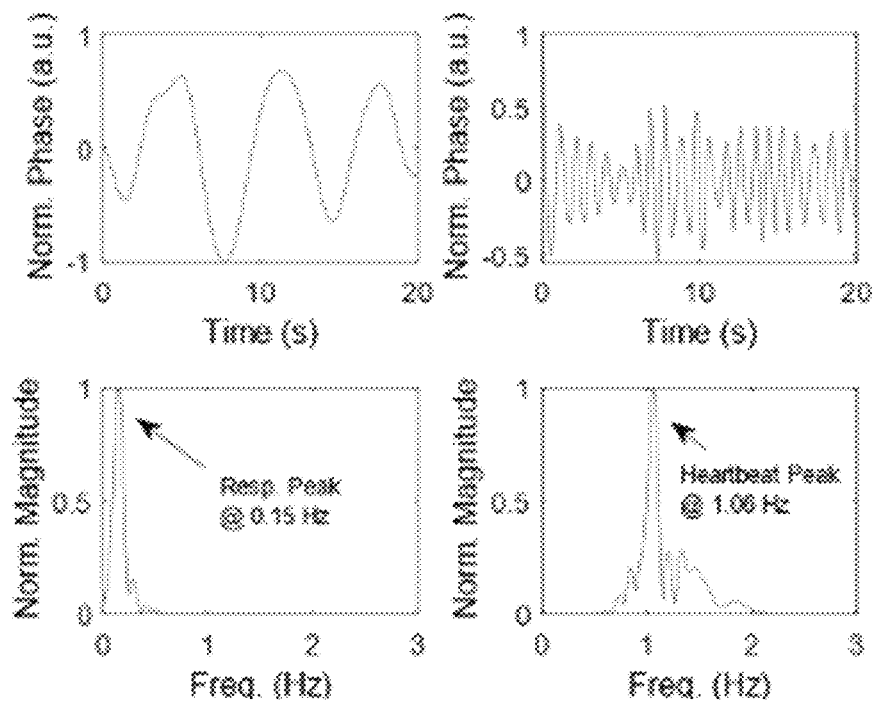
FIG. 4G shows exemplary respiration (left) and heartbeat (right) signals of the first subject and corresponding spectra measured with the aid of a medical reference device.
Figure 4H:
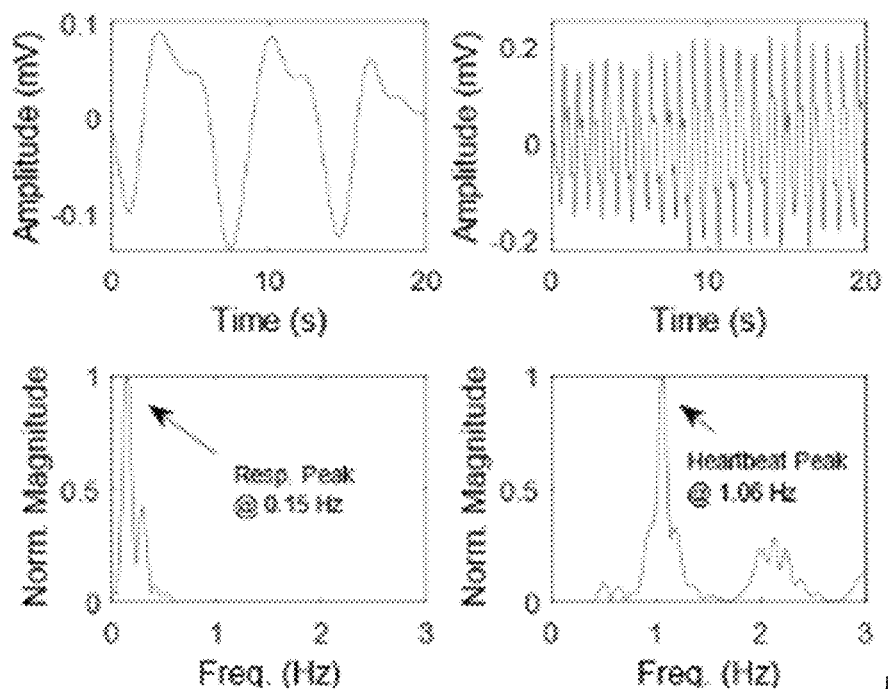
FIG. 4H shows exemplary respiration (left) and heartbeat (right) signals of the second subject and corresponding spectra measured with the aid of a medical reference device.

FIG. 4E and FIG. 4F show the respiration and heartbeat signals of the two subjects with the corresponding spectra from which the rates are extracted. Those results are in fair agreement with the rates obtained from the references and shown in FIG. 4G and FIG. 4H. In this example, for subject 1, the estimated heartrate of subject 1 and the corresponding reference rate differ of only 0.02 Hz which is a clinically acceptable difference. The vital signs signal are filtered using wavelet decomposition. However, other approaches can be used, for example, using standard filters.

Another approach can be generating the analytic signals of $\hat{y}(t)$ by using the Hilbert transform:

$$\hat{y}^*(t) = \mathcal{H}(\hat{y}(t)) = a_r \sin(2\pi f_r t) + a_h \sin(2\pi f_h t), \tag{4}$$

wherein $\mathcal{H}$ denotes the Hilbert transform operator.

The analytic signal $\hat{y}^A(t)$ is:

$$\hat{y}^A(t) = \hat{y}(t) + j\hat{y}^*(t) = a_r e^{j2\pi f_r t} + a_h e^{j2\pi f_h t}, \tag{5}$$

The second last equation can be rewritten as:

$$\hat{y}^A = \psi^H f, \tag{6}$$

wherein $$f = [e^{j2\pi f_{min}t}, e^{j2\pi (f_{min}+\Delta f)t}, \ldots, e^{j2\pi f_{max}t}]^H, \text{ and}$$

$\Psi$ is an unknown vector which indicates the complex weights of the sinusoidal candidates in f, and $\Delta f$ is the resolution of the discretized dictionary.

The estimation of $\Psi$ from $\hat{y}^A(t)$ is a convex optimization problem of the form:

$$\min_{\Psi} \|\hat{y}^A - \Psi^H f\|_2^2 + \zeta \|\Psi\|_1, \quad (7)$$

wherein $\zeta$ denotes a positive real value and the l–1 norm term is added to preserve the sparsity of the weight vector.

Since the respiration rate is normally within the 0.1–0.8 Hz range and the respiration signal is stronger than the heartbeat signal, it can be assumed:

$$y(t) \approx y_r(t) = a_r e^{j2\pi f_r t}. \quad (8)$$

Therefore, one can temporally focus on frequencies between 0.1 and 0.8 Hz to reconstruct $\hat{y}^A(t)$ and to estimate the respiration rate. The heartbeat signal $\hat{y}_h(t)$ can be estimated by subtracting the reconstructed respiration signal $\hat{y}_r(t)$ from $\hat{y}^A(t)$. The corresponding heartbeat can be obtained with the same methodology of the second last equation.

Again, with respect to the above-mentioned singular value decomposition, the target existence probability, the independent component analysis, the linear demodulation, and the automatic localization, the corresponding steps thereof should be discussed in greater detail in the following.

In this context, an array signal model is introduced: The received signal sR(t,m) over a multipath channel can be modelled as the convolution between the channel impulse response h(t,m) and the transmitted signal sT(t).

Considering a single target, it can be expressed as:

$$s_R(tm) = \sum_i s_T(t) * h_i(t,m) = \sum_i \sum_l \beta_{i,l} \cdot s_T(t - \tau_{i,l}(m)) \quad (9)$$

with $$s_T(t) = a_T e^{j2\pi \int_0^t (f_0 + \rho t) dt} = a_T e^{j2\pi (f_0 + \rho/2 t) t} \quad (10),$$

$$\tau_{i,l}(m) = \begin{cases} 2\dfrac{d_{i,l} + y_i(m)}{c_0}, & \text{subject} \\ 2\dfrac{d_{i,l}}{c_0}, & \text{clutter} \end{cases} \quad (11)$$

wherein aT is the complex amplitude indicating the amplitude of the chirp and its initial phase, $\rho = B/T$ is the sweeping rate, m is the slow time index, i is the index corresponding to the i-th target/object, d is the path distance, y(m) is the chest surface displacement, $c_0$ is the speed of light, and * is the convolution operator.

The baseband signal sB(t,m) can be modelled as:

$$s_B(t,m) = s_T(t) \cdot s_R^*(t,m) = \sum_i \sum_l \beta_{i,l}^* a_T^2 e^{j2\pi(f_0 \tau_{i,l}(m) - \frac{\rho}{2}\tau_{i,l}^2(m) + \rho \tau_{i,l}(m) t)} \approx \quad (12)$$

$$\sum_i \sum_l \beta_{i,l}^* a_T^2 e^{j2\pi f_0 \tau_{i,l}(m)} \cdot e^{j2\pi \rho \tau_{i,l}(m) t}$$

where the superscript * indicates the complex conjugate operation. The quadratic term is neglected because $\tau_{i,j}(m)$ is close to zero. The digitized baseband signal can be expressed as:

$$s_B(n,m) \approx \Sigma_i \Sigma_l \beta_{i,l}^* a_T^2 e^{j2\pi f_0 \tau_{i,l}(m)} \cdot e^{j2\pi \rho \tau_{i,l}(m) n T_f} \quad (13)$$

where n is the fast time index and Tf is the fast time sampling time (i.e., ADC sampling rate). After performing FFT in fast time, the frequency domain signal X(k,m) becomes:

$$X(k,m) = \quad (14)$$

$$\mathcal{F}\{s_B(n,m) \cdot w(n)\} = \sum_i \sum_l e^{j2\pi f_0 \tau_{i,l}(m)} \cdot \beta_{i,l}^* a_T^2 W\left(\frac{2\pi k}{K} - 2\pi \rho \tau_{i,l}(m)\right) \approx$$

$$\sum_i \sum_l e^{j2\pi f_0 \tau_{i,l}(m)} \cdot \beta_{i,l}^* a_T^2 W_{i,l}(k)$$

with $$W_{i,l}(k) = W\left(\frac{2\pi k}{K} - 2\pi \rho \tau_{i,l}\right), \quad (15)$$

wherein F is the Fourier transform operator, w(n) is a rectangular window function in fast time, w(n) and W(k) are a Fourier pair. Since the rectangular window in frequency domain is a sinc function with gradients close to zero around $2\pi\rho\tau_{i,l}$ the frequency domain window function $W_{i,j}(k)$ can be considered as a fixed one in slow time.

Assuming P subjects and Q static clutter in a room, equation (14) can be written as:

$$X(k,m) = \sum_{i=1}^{P} a_i(k) e^{j\phi_i(m)} + c(k) \quad (16)$$

with $$a_i(k) = \sum_l e^{j\frac{4\pi f_0 d_{i,l}}{c_0}} \cdot \beta_{i,l}^* a_T^2 W_{i,l}(k), \quad (17)$$

$$c(k) = \sum_{i=P+1}^{P+Q} \sum_l e^{j\frac{4\pi f_0 d_{i,l}}{c_0}} \cdot \beta_{i,l}^* a_T^2 W_{i,l}(k), \quad (18)$$

$$\phi_i(m) = \frac{4\pi f_0}{c_0} y_i(m), \quad (19)$$

wherein $\phi_i(m)$ is the Doppler shift caused by the vital signs on the FMCW signal. The observation signal X(k,m) is a dual-variable function of k and m and forms a two-dimensional observation matrix X with factorization $$X = HS + C \quad (20),$$

wherein $$H = \begin{bmatrix} a_1(0) & \cdots & a_P(0) \\ \vdots & \ddots & \vdots \\ a_1(L-1) & \cdots & a_P(L-1) \end{bmatrix} : L \times P, \quad (21)$$

$$S = \begin{bmatrix} e^{j\phi_1(0)} & e^{j\phi_1(1)} & \cdots & e^{j\phi_1(M-1)} \\ \vdots & \vdots & \ddots & \vdots \\ e^{j\phi_P(0)} & e^{j\phi_P(1)} & \cdots & e^{j\phi_P(M-1)} \end{bmatrix} : P \times M, \quad (22)$$

and $$C = [c(0) \ldots c(L-1)]^T \cdot 1^T : L \times M \quad (23),$$

Here, 1 is a length M all-ones column vector. In presence of additive noise, the data model becomes as in equation (2) mentioned above. The next step is to remove C in X using a projection (or centering matrix) P such that CP=0. This requires $1^T P=0$, where 1 is a vector with all entries equal to 1, so that $$P = I - 1(1^T 1)^{-1} 1^T, \quad (24)$$

wherein I is an identity matrix. The result is:

$$XP = HSP + CP + NP = HSP + N, \quad (25)$$

wherein the noise statistics remain the same due to their zero mean nature. Equation (25) is especially equivalent to the mentioned above equation (3) with:

$$\bar{X} = XP, \quad (26)$$

$$\bar{S} = SP. \quad (27)$$

Now, with respect to the singular value decomposition, it is noted that the noise is reduced by applying singular value decomposition (SVD) to equation (3) as:

$$\bar{X} = H\bar{S} + N = U \cdot \sum \cdot V^H = [U_s \ U_n] \begin{bmatrix} \sum_s & 0 \\ 0 & \sum_n \\ 0 & 0 \end{bmatrix} \begin{bmatrix} V_s^H \\ V_n^H \end{bmatrix}, \quad (28)$$

wherein U denotes an L×L unitary matrix containing left singular vectors, V is an M×M unitary matrix containing right singular vectors, and Σ is a diagonal matrix containing all the singular values.

The first P columns in U and V are denoted respectively as $U_s$ and $V_s$ while the rest columns as $U_n$ and $V_n$ respectively. As noise is assumed to be uncorrelated to the sources in $\bar{S}$, the columns of $V_s$ span the same subspace as the rows in $\bar{S}$ and the columns of $V_n$ span the noise space.

Therefore, $V_s$ can be expressed as the following linear transform:

$$V_s = A\bar{S}, \quad (29)$$

wherein A is a P×P square mixing matrix. Therefore, by taking the signal space, one cannot only remove the noise falling into the null space, but also pre-whiten the data based on the second order statistic.

With respect to the target existence probability, it is noted that in order to estimate P, and therefore to determine $V_s$, we calculate the signal-to-noise ratio (SNR) of the uncorrelated sources in V. An exemplary calculation of the SNR is explained in the following.

A spectrum of a canonical radar-based vital signs signal consists essentially of the respiration fundamental, which is the dominant component of the signal, of one or two decreasing in magnitude respiration harmonics, and of the very small heartbeat fundamental.

We consider as signal power the power within the fundamental and its first harmonic while the rest of the spectrum is considered as signal noise. The first P sources of V (i.e., first P columns) produce a high SNR and indicate $V_s$ while the remaining sources have very low SNR and indicate $V_n$.

Furthermore, also other checks may be performed on the spectrum's local maxima:

(1) if the peak, which should indicate the respiration rate, is outside the typical medical ranges, it is concluded that this source is noise;

(2) we determine the ratio of strongest peak and its first harmonic.

We consider as noise any source producing a ratio less than 2. In fact, in the canonical spectrum, the two highest peaks indicate the respiration fundamental and its first harmonic and their ration is always greater than a factor 2.

In those two situations, we fix the SNR to 0 dB. The last operation is to scan the obtained SNR profile starting from the first estimation and stopping when the first descending order uncorrelated source produced an SNR below a threshold. The latter source indicates the starting of $V_n$ while the previous ones are the $V_s$ sources corresponding to the P subjects.

It is further noted that with the aid of the target existence probability, we especially extract the Doppler signals in order to first determine the number of targets and then to estimate their vital signs and location. The first step is to reduce the noise by applying the singular value decomposition to $\bar{X}$. It results is used to determine the number of persons P (target existence probability) in the monitored environment. We specify that in real environments P cannot be determined by simply calculating the rank of $\bar{X}$. Knowing the number of targets, the singular value decomposition result is further processed by the independent component analysis in order to estimate the sources $\hat{S}$.

Again, it is noted that the foregoing explanations show an exemplary way to calculate the SNR. For instance, the signal power can be calculated from the fundamental to the second harmonic of the respiration or other way. Further exemplarily, the checks on the peaks could not be necessary may be a preferred implementation form.

With respect to the independent component analysis, it is noted that in equation (29), the rows of $\bar{S}$ are the underlying independent sources, A is a mixing matrix, and the rows of $V_s$ are the mixtures of the sources in $\bar{S}$.

Since the first step of the independent component analysis, i.e., the pre-whitening, has been done by the singular value decomposition, the estimation of $\bar{S}$ only needs one more step, searching for the unmixing matrix W such that the de-mixed sources have the largest statistical independence:

$$\hat{S} = W^H V_s. \quad (30)$$

Based on the central limit theorem, the sum of independent random variables tends to a Gaussian distribution. This gives the inspiration that the estimated independent sources should tend to be as non-Gaussian distributed as possible. There are various ways to measure non-Gaussianity.

With respect to the phase demodulation or the linear demodulation, respectively, it is noted that especially based on a small angle approximation, preferably valid for sub-10 GHz radar, a source can be approximated as:

$$s(t) = e^{j\phi(t)} \approx 1 + j\phi(t) - \frac{\phi^2(t)}{2}, \quad (31)$$

wherein $\phi(t)$ is the phase (Doppler) shift caused by the vital signs. Especially after DC removal, we observe that the imaginary part is more powerful than the real part:

$$\bar{s}(t) \approx j\phi(t). \quad (32)$$

The vital signs information or signal ŷ(t) can be extracted applying the linear demodulation to the estimated source ŝ(t) and it can be expressed as:

$$\hat{y}(t) = \hat{s}_{LIN}(t)\frac{\lambda_0}{4\pi}, \tag{33}$$

wherein $\hat{s}_{LIN}(t)$ is the estimated source after the linear demodulation and $\lambda 0$ is the wavelength corresponding with the start frequency of the chirp. If the demodulation is performed correctly, equation (33) is equivalent to the motion of the chest surface x(t) caused by the vital signs. This movement can be modeled as the sum of two sinusoidal functions as:

$$x(t) = x_r(t) + x_h(t) = a_r \cos(2\pi f_r t) + a_h \cos(2\pi f_h t), \tag{34}$$

wherein xr(t) and xh(t) indicate respectively the mechanical chest surface displacements caused by respiration (expansion of thorax and lungs) and heart contractions; ar and ah are the maximum mechanical displacements caused by the lungs and heart on the chest surface (with typical amplitudes around 4-12 mm and 0.1-0.5 mm, respectively), and fr and fh are the vital signs frequencies which represent the information to be extracted.

Finally, with respect to the automatic localization, it is noted that in order to locate the targets and to remove the order ambiguity, knowing the observation matrix $\overline{X}$ and the estimated source matrix $\hat{S}$, we determine $\hat{H}$ by minimizing the residual error $\|\overline{X} - \hat{H}\hat{S}\|_2^2$.

However, due to the path loss, the observation vectors (rows) in $\overline{X}$ have unequal power. To better balance the residual errors, it is possible to perform a row-wise normalization on $\overline{X}$.

Assuming $\overline{\overline{X}}$ is the normalized version of $\overline{X}$ and $\overline{A}$ is the scaling matrix, the following is obtained:

$$\overline{\overline{X}} = \overline{A}\overline{X} = \overline{A}H\hat{S} = \overline{H}\hat{S}. \tag{35}$$

In order to preserve the sparsity of the multipath propagation channel, the final cost function should be $$\min_{\overline{H}}\|\overline{\overline{X}} - \overline{H}\hat{S}\|_2^2 + \zeta\|\overline{H}\|_1, \tag{36}$$

wherein $\zeta$ is the penalty coefficient which represents a trade-off between the residual error and the sparsity. As the scaling matrix $\overline{A}$ is known, it is obtained $$\hat{H} = \overline{A}\overline{H}. \tag{37}$$

Figure 5A:
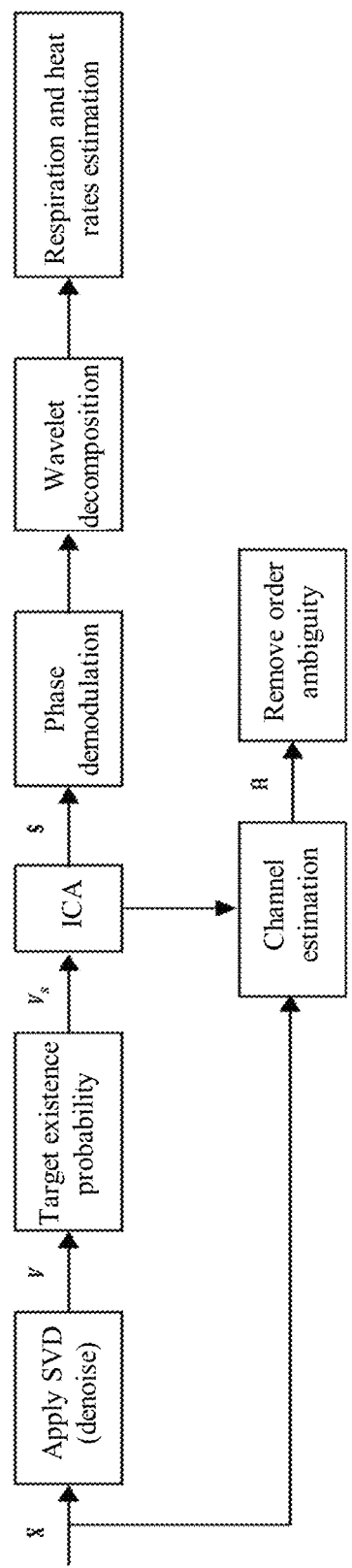
FIG. 5A shows a flow chart of a further exemplary embodiment of the inventive method on the basis of FIG. 4A.
Figure 5B:
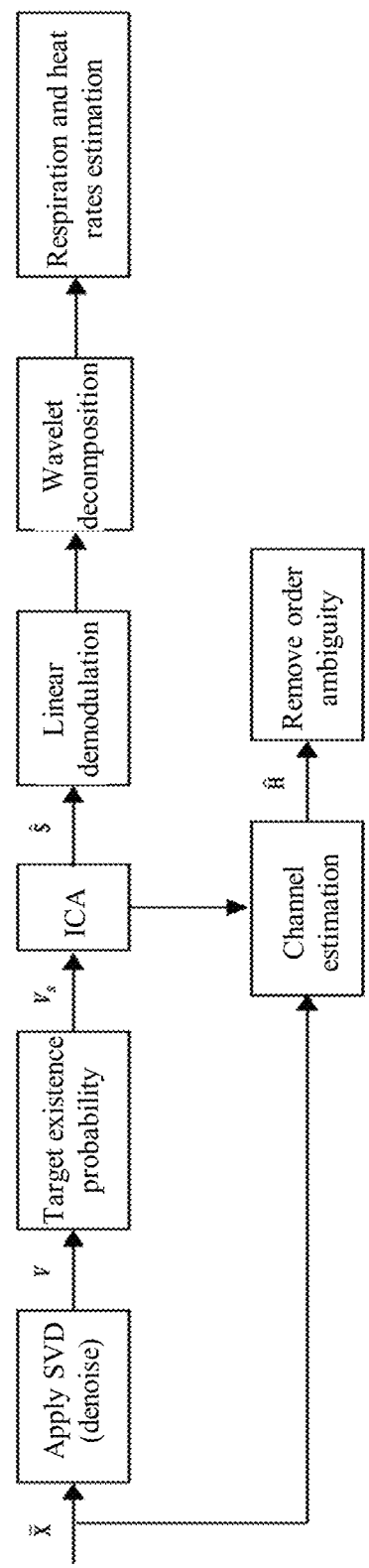
FIG. 5B shows a flow chart of a further exemplary embodiment of the inventive method on the basis of FIG. 4A.

Again, with respect to the target existence probability, two further exemplary embodiments being based on the embodiment according to FIG. 4A are shown by FIG. 5A and FIG. 5B.

As it can been from said FIG. 5A and FIG. 5B, in both cases, the steps for estimating the target existence probability have been inserted between the singular value decomposition and the independent component analysis. In addition to this, whereas the embodiment of FIG. 5A uses a phase demodulation after the independent component analysis, a linear demodulation is used instead according to FIG. 5B.

Figure 5C:
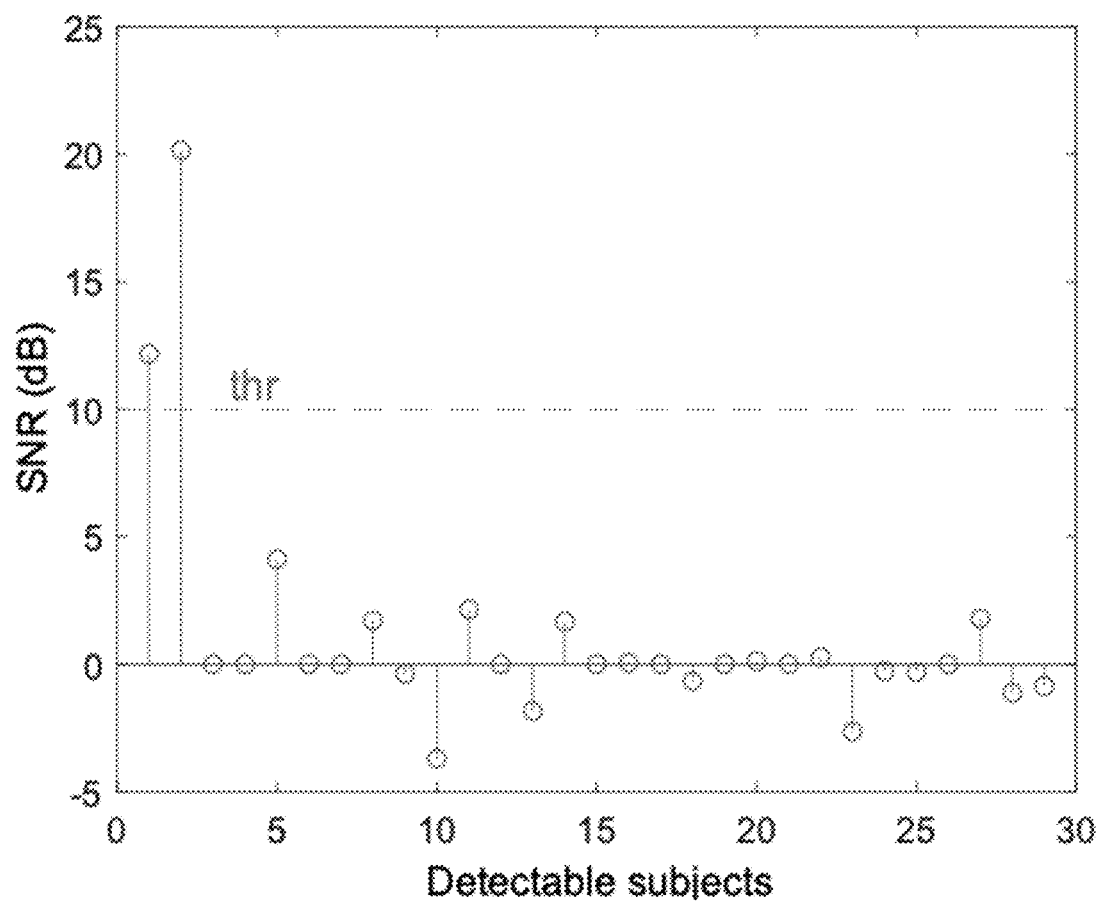
FIG. 5C shows an exemplary estimated target existence probability in terms of signal-to-noise ratios of the uncorrelated sources obtained after the singular value decomposition.

Moreover, FIG. 5C illustrates an exemplary estimated target existence probability in terms of signal-to-noise ratios of the uncorrelated sources obtained after the singular value decomposition.

In this context, as it can be seen, fixing a threshold thr (dashed line in FIG. 5C), from the stem plots, it results clear that there are exemplarily two subjects in the respective monitored environment.

Figure 5D:
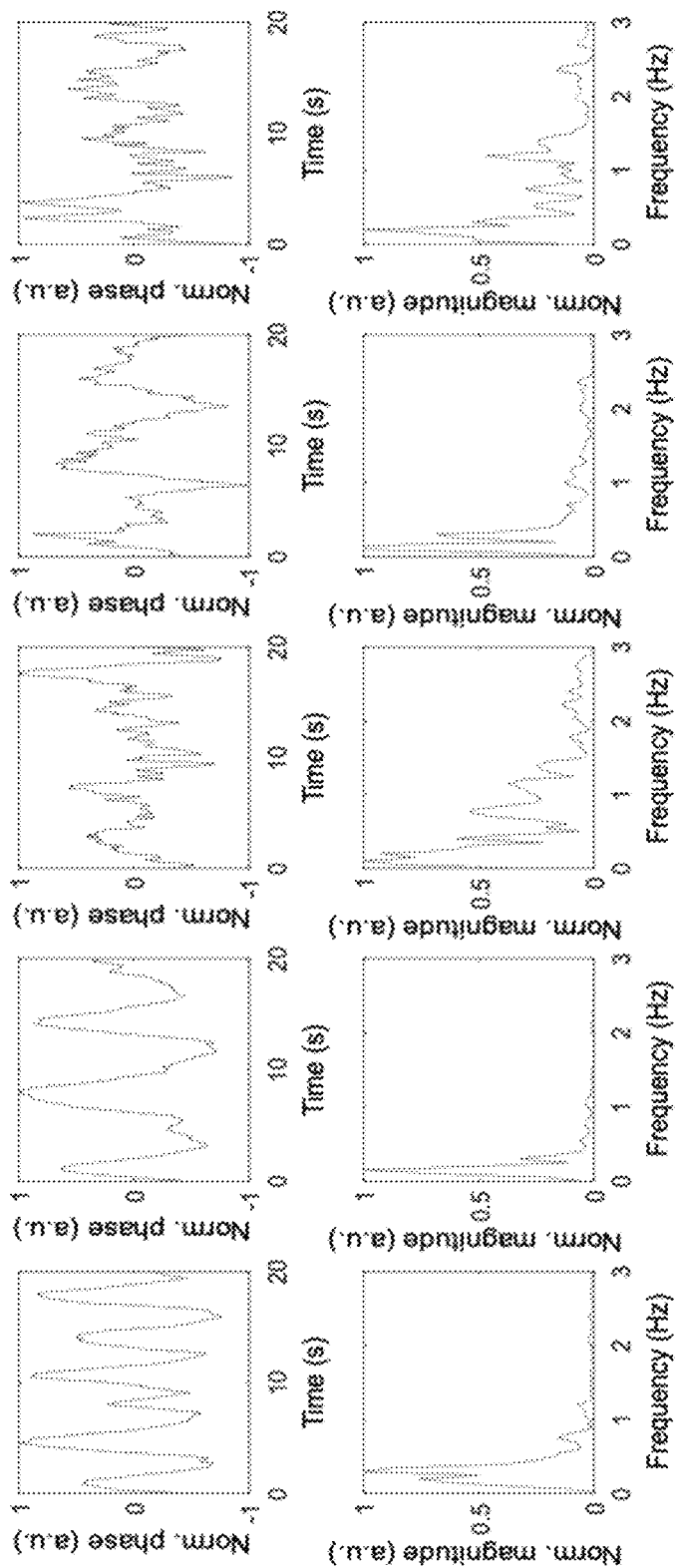
FIG. 5D shows exemplary phase information and relative spectra of the first five sources after singular value decomposition when two subjects are present in the monitored environment.

Finally, FIG. 5D shows exemplary phase information and relative spectra of the first five sources after singular value decomposition when two subjects are present in the respective monitored environment.

In this context, it is noted that a visual check of the time domain signals clearly reveals that the first two sources resemble the typical radar-based vital signs signals.

In addition to this, these sources result less noisy than the other three. This is also confirmed by the spectra plots. In fact, the first two spectra consist essentially of the respiration fundamental, which is the dominant component of the signal, and of its harmonic, while the other three spectra contain several components.

We can notice that, although noisy, the fourth source could be misleading as it might resemble the second one. However, a check of the fundamental-harmonic ratio resolves the ambiguity. In fact, in a normal radar-based vital signs signals this ratio is always greater than a factor 2 (see the spectrum of the second source).

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The invention claimed is:

1. A method for automatic multi-object localization and/or vital sign monitoring, the method comprising:
   transmitting a radar signal;
   receiving a corresponding transmitted radar signal in order to form a corresponding observation matrix ($\overline{X}$);
   reducing noise by applying singular value decomposition to the observation matrix ($\overline{X}$);
   processing the result of the singular value decomposition by an independent component analysis in order to estimate corresponding sources ($\hat{S}$), wherein each source is an observed source of vital sign information;
   estimating propagation channels (H) of the estimated sources ($\hat{S}$) by minimizing corresponding residual error ($\|\overline{X} - \hat{H}\hat{S}\|_2^2$) using the observation matrix ($\overline{X}$) and the estimated sources ($\hat{S}$), wherein each propagation channel is a representation of how a signal is transmitted from the corresponding source to the receiver; and
   locating the respective objects using the estimated sources ($\hat{S}$) and estimated propagation channels (H).

2. The method according to claim 1,
   wherein before the independent component analysis, the method further comprises estimating a number of respective targets, by calculating the signal-to-noise ratio of respective uncorrelated sources in the result of the singular value decomposition.

3. The method according to claim 1,
wherein the method further comprises removing respective order ambiguity using the estimated propagation channels ($\hat{H}$).

4. The method according to claim 1,
further comprising performing a phase demodulation with respect to the estimated sources ($\hat{S}$).

5. The method according to claim 4,
further comprising extracting the respective vital sign information or signal ($\hat{y}(t)$) from the time domain signals ($\hat{s}(t)$) of the estimated sources ($\hat{S}$) after the phase demodulation.

6. The method according to claim 5,
wherein the extracting is performed using the following equation:

$$\hat{y}(t) = \hat{s}(t)\frac{\lambda_0}{4\pi},$$

wherein $\lambda_0$ denotes the corresponding wavelength at the first frequency of a respective chirp signal, and
wherein $\pi$ denotes the constant Pi.

7. The method according to claim 5,
further comprising obtaining corresponding respiration and heartbeat signals by performing a filtering operation with respect to the respective vital sign information or signal ($\hat{y}(t)$).

8. The method according to the claim 7,
further comprising estimating corresponding heart rates by performing a frequency transform with respect to the respective respiration and heartbeat signals.

9. The method according to claim 8,
wherein the frequency transform comprises or is a fast Fourier transform.

10. The method according to claim 5,
further comprising obtaining the corresponding respiration and heartbeat signals by performing a wavelet decomposition with respect to the respective vital sign information ($\hat{y}(t)$).

11. The method according to claim 5,
further comprising obtaining the corresponding respiration and heartbeat signals by performing a Hilbert transform and/or further convex optimization steps with respect to the respective vital sign information or signal ($\hat{y}(t)$).

12. The method according to claim 1,
wherein the radar signal comprises a chirp signal.

13. The method according to claim 1,
wherein the radar signal originates from a frequency-modulated continuous wave radar.

14. A system for automatic multi-object localization and/or vital sign monitoring, the system comprising:
a transmitter; and
a receiver; and
a processor,
wherein the transmitter is configured to transmit a radar signal, the receiver is configured to receive a corresponding transmitted radar signal in order to form a corresponding observation matrix ($\overline{X}$), and
wherein the processor is configured to reduce noise by applying singular value decomposition to the observation matrix ($\overline{X}$), to process the result of the singular value decomposition by an independent component analysis in order to estimate corresponding sources ($\hat{S}$), wherein each source is an observed source of vital sign information, to estimate propagation channels (H) of the estimated sources ($\hat{S}$) by minimizing corresponding residual error ($\|\overline{X}-H\hat{S}\|_2^2$) using the observation matrix ($\overline{X}$) and the estimated sources ($\hat{S}$), wherein each propagation channel is a representation of how a signal is transmitted from the corresponding source to the receiver, and to locate the respective objects using the estimated sources ($\hat{S}$) and estimated propagation channels (H).

15. A non-transitory computer-readable medium storing a computer program, which, when read and executed by a computer causes the computer to perform a method of automatic multi-object localization and/or vital sign monitoring, the method comprising:
transmitting a radar signal;
receiving a corresponding radar signal in order to form a corresponding observation matrix ($\overline{X}$);
reducing noise by applying singular value decomposition to the observation matrix ($\overline{X}$);
processing the result of the singular value decomposition by an independent component analysis in order to estimate corresponding sources ($\hat{S}$), wherein each source is an observed source of vital sign information;
estimating propagation channels (H) of the estimated sources ($\hat{S}$) by minimizing corresponding residual error ($\|\overline{X}-H\hat{S}\|_2^2$) using the observation matrix ($\overline{X}$) and the estimated sources ($\hat{S}$), wherein each propagation channel is a representation of how a signal is transmitted from the corresponding source to the receiver; and
locating the respective objects using the estimated sources ($\hat{S}$) and estimated propagation channels (H).

* * * * *